United States Patent [19]
Allen

[11] Patent Number: 5,658,335
[45] Date of Patent: Aug. 19, 1997

[54] SPINAL FIXATOR

[75] Inventor: Ronald C. Allen, Foster City, Calif.

[73] Assignee: Cohort Medical Products Group, Inc., Hayward, Calif.

[21] Appl. No.: 401,212

[22] Filed: Mar. 9, 1995

[51] Int. Cl.$^6$ ............................................. A61F 2/44
[52] U.S. Cl. ................................... 623/17; 606/61
[58] Field of Search ............................ 623/16, 17, 18; 606/60, 61, 62, 63, 64

[56] References Cited

U.S. PATENT DOCUMENTS

| | | |
|---|---|---|
| 3,741,205 | 6/1973 | Markolf et al. . |
| 4,289,123 | 9/1981 | Dunn . |
| 4,309,777 | 1/1982 | Patil . |
| 4,401,112 | 8/1983 | Rezaian . |
| 4,502,160 | 3/1985 | Moore et al. . |
| 4,502,161 | 3/1985 | Wall . |
| 4,553,273 | 11/1985 | Wu ............................... 623/17 X |
| 4,599,086 | 7/1986 | Doty ............................. 623/17 |
| 5,015,247 | 5/1991 | Michelson .................. 623/17 X |
| 5,123,926 | 6/1992 | Pisharodi ..................... 623/17 |
| 5,458,641 | 10/1995 | Ramirez Jimenez ........ 623/17 |
| 5,534,029 | 7/1996 | Shima ........................ 606/61 X |
| 5,534,031 | 7/1996 | Matsuzaki et al. ......... 606/61 X |

FOREIGN PATENT DOCUMENTS

| | | | |
|---|---|---|---|
| 1107854 | 8/1984 | U.S.S.R. | ........................ 623/17 |
| 1560184 | 4/1990 | U.S.S.R. | ........................ 623/17 |
| 9426213 | 11/1994 | WIPO | ........................ 623/17 |

*Primary Examiner*—Mary Beth Jones
*Attorney, Agent, or Firm*—James E. Eakin

[57] ABSTRACT

An adjustable spinal fixator for insertion between adjacent vertebrae comprises a contoured housing defining convex edges to fit within the concavity of the vertebral body. An externally threaded core extends through the housing, and a pair of internally threaded nut assemblies attach to the core member. Four crown members with teeth are separately mounted within the housing and retract and variably extend with the movement of the movable nuts on the core member. Two of the crown members extend and retract from the top of the housing, and the remaining two crown members extend and retract from the bottom of the housing. The spinal fixator is positioned between adjacent vertebrae with the crown members retracted so that the teeth are below the convex edges of the housing. Following placement, the crown members are extended outwardly from the top and bottom of the housing by rotation of the core member which causes the teeth to penetrate the bone at an angle to secure the spinal fixator in position. Preferably, a bone graft surrounds the implanted spinal fixator which defines apertures for bony ingrowth. Several sizes of spinal fixators exist to accommodate differing anatomies of the spine.

3 Claims, 4 Drawing Sheets

SPINAL FIXATOR

FIELD OF THE INVENTION

The present invention relates to apparatus for immobilizing the spine, or a portion of the spine. More particularly, the invention relates to a contoured, adjustable spinal fixator for insertion between damaged or resected vertebrae.

BACKGROUND OF INVENTION

Spinal stabilization, or immobilization, may become necessary during treatment of a number of illnesses or injuries involving the spinal column. Immobilization of the spine may be required to treat spinal fractures, infections affecting the spinal column, tumors associated with the spinal column, and any other injury or illness causing spinal instability. Instability of the spine requires intervention to relieve pain and to maintain neurological function.

Surgical intervention is frequently necessary to immobilize spinal vertebrae, and is particularly suitable in those cases where surgical intervention is required in any event to treat the underlying disease processes, for example, tumors of the spine and vertebral necrosis caused by infectious agents. In such cases, the damaged or necrotic bone is removed, and the remaining bone is resected.

Surgical methods for spinal immobilization may include the placement of bone grafts, or synthetic polymers, to replace necrotic, and/or diseased bone. Such materials may also be implanted in the intervertebral space between adjacent vertebrae to replace damaged discs and immobilize the surrounding vertebrae. Bone grafts require at least several months for fusion, thereby requiring the wearing of extremely uncomfortable and restrictive external stabilization devices, and bone grafts may provide insufficient stabilization in those situations when the graft is not completely successful, or where ongoing treatment interferes with fusion of the graft. Synthetic polymer implants generally also require metal pins or rods to compensate for bonding difficulties, and such implants are difficult to implant and subject to stress fractures. Additionally, the pins may break thereby eliminating any stability produced by the polymer, and the polymer may then move from its implanted position.

Metal spinal fixators, in addition to the metal pins discussed above, are known in the prior art. Such fixators may include bone screws, rods, plates, a combination of screws and plates, and a combination of rods and screws. Bone screws, rods and plates immobilize a vertebra by connecting it to an adjacent vertebra. The rods and plates are generally placed on the outside of the lateral portion of the vertebrae, and the screws are used to secure the position of the plates and rods. One such device is shown in U.S. Pat. No. 3,741,205 which discloses an open frame, rectangular plate secured to the outer anterior aspect of the vertebrae with pins. Another device utilizing rods attached through brackets which are attached by screws to the lateral aspect of the vertebrae is disclosed in U.S. Pat. No. 4,289,123. Such devices are inherently limited because the attachment to the bone generally is made with small screws or pins and is thereby subject to displacement from movement of the spine.

Spinal fixators for insertion in the space between vertebrae are known in the prior art. Such devices are designed to immobilize the spine and to maintain the typical distance between adjacent vertebrae thereby decompressing the spine to relieve pressure on the spinal cord.

One such spinal fixator for insertion between vertebrae is described in U.S. Pat. No. 4,401,112 which teaches a turnbuckle device with terminal spikes. A plate is attached to the turnbuckle and to the anterior aspect of the two adjacent vertebrae. Another spinal fixator is described in U.S. Pat. No. 4,599,086 which discloses a body having two retractable pins inserted between the vertebrae and secured in position with an externally mounted plate and screws.

In addition to the spinal fixators discussed above, other devices exist which are used to replace an intervertebral disc or a meniscus between a joint. A replacement for an intervertebral disc is disclosed in U.S. Pat. No. 4,309,777, and comprises a spring operated insert secured to the adjacent vertebrae with spikes. A resilient, rubber meniscus replacement is shown in U.S. Pat. No. 4,502,161.

A heretofore unmet needs exists for an adjustable spinal fixator that may be easily inserted between two vertebrae for immobilization thereof without the need for additional screws and/or plates to secure the position of the fixator.

SUMMARY OF THE INVENTION WITH OBJECTS

A spinal fixator for insertion between adjacent vertebrae and embodying the principles of the present invention comprises a contoured housing dimensioned to fit in the concavity of the vertebral body. A core member extends through the housing, and a pair of movable nut assemblies are attached to threads on the core member. Four crown members are mounted within the housing to extend and retract with the movement of the movable nut assemblies on the core member. Two of the crown members extend and retract from the top of the housing, and the remaining two crown members extend and retract from the bottom of the housing. Teeth extend outwardly from the surface of the four crown members and at an angle away from midline. The spinal fixator is positioned between the adjacent vertebrae with the teeth retracted. Following placement, the crown members are variably extended outwardly from the top and bottom of the housing by rotation of the core member which causes the teeth to penetrate the bone to secure the spinal fixator in position. Preferably, a bone graft surrounds the implanted spinal fixator which defines apertures for bony ingrowth. Several sizes of spinal fixators exist to accommodate differing anatomies of the spine.

A general object of the invention is to provide a spinal fixator that overcomes the drawbacks and limitations of the prior art.

A specific object of the invention is to provide a spinal fixator with a convex housing which fits within the contours of the concave vertebral bodies, and is cupped by the bony edges of the bodies, enabling secure placement without the necessity for additional screws or plates.

Another specific object of the present invention is to provide a spinal fixator having teeth positioned to enter the vertebral body at an angle away from midline to prevent displacement of the fixator during spinal flexure and/or extension.

Yet another specific object of the present invention is to provide an adjustable spinal fixator having retractable teeth to adjust the height of the fixator to enable pre-positioning between two adjacent vertebrae without scraping of the vertebral body surfaces during positioning.

Yet one more specific object of the present invention is to provide a spinal fixator with a plurality of apertures to facilitate bony ingrowth to further stabilize the fixator.

Still one more specific object of the present invention is to provide adjustable spinal fixators of various sizes and having selectable extension lengths.

Still another specific object of the present invention is to provide a spinal fixator made from a lightweight material, preferably titanium, which enhances postoperative radiographic evaluation.

One more specific object of the present invention is to provide a spinal fixator with four, separate, extendable crown members thereby enabling engagement by the teeth of one crown member at a different height than engagement by others of the three remaining crown members, the four separate crown members enabling the fixator to better accommodate to the contours of the vertebrae bodies.

These and other objects, advantages and features of the present invention will become more apparent upon considering the following detailed description of preferred embodiments, presented in conjunction with the accompanying drawings.

BRIEF DESCRIPTION OF THE DRAWINGS

Figure 1:
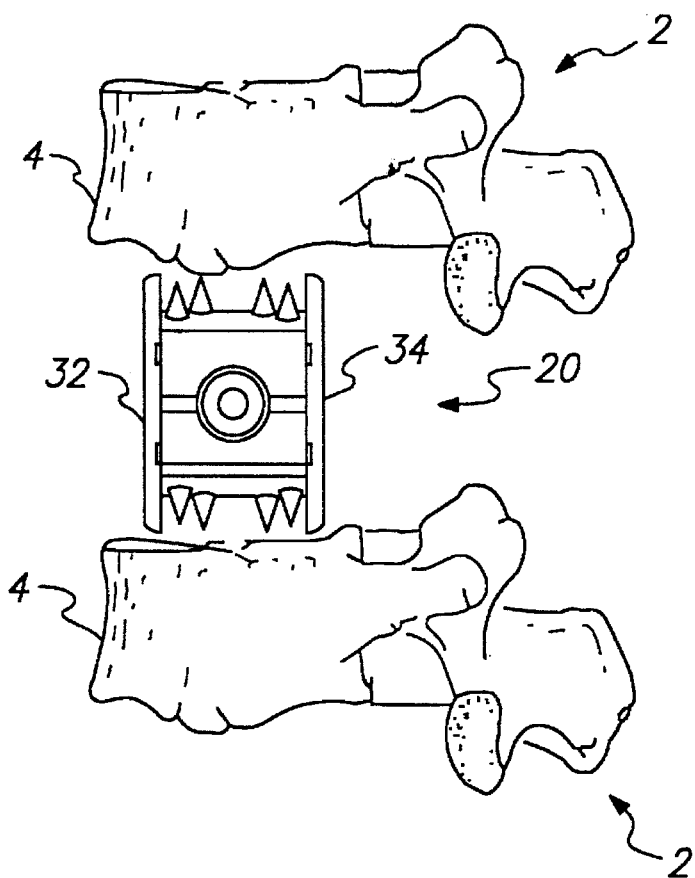

IN THE DRAWINGS:

FIG. 1 is a lateral view of a spinal fixator embodying the principles of the present invention and shown in its fully retracted position between two vertebrae prior to fixation to the vertebrae.

Figure 2:
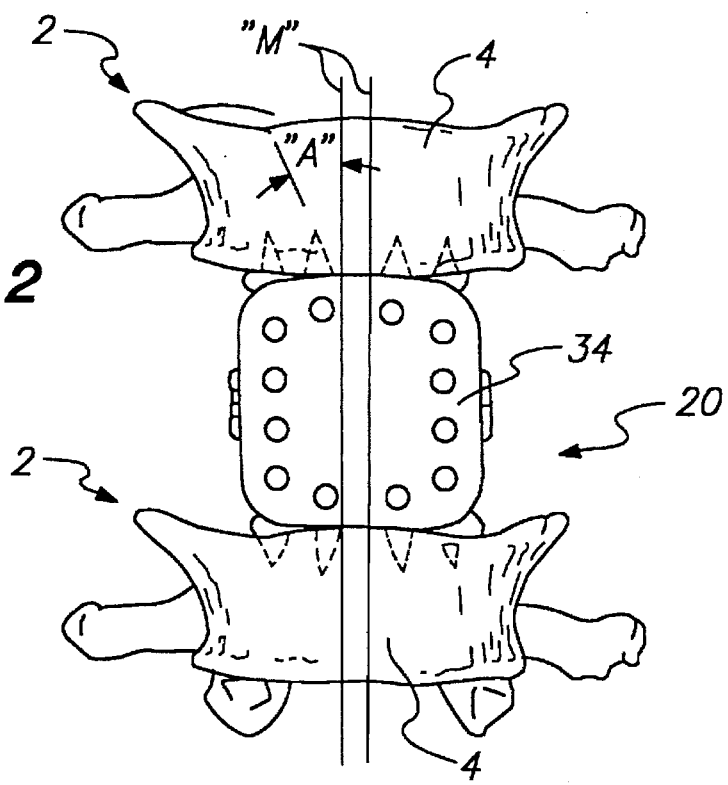

FIG. 2 is a posterior view of the spinal fixator of FIG. 1 shown following fixation with the teeth implanted in the bodies of the two vertebrae which surround and cup the spinal fixator therebetween.

Figure 3:
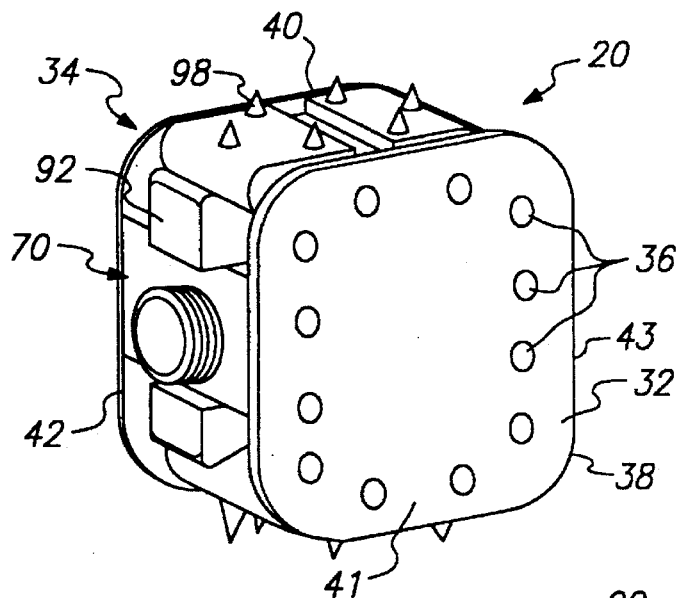

FIG. 3 is a perspective view of a spinal fixator with the crown portions partially retracted.

Figure 4:
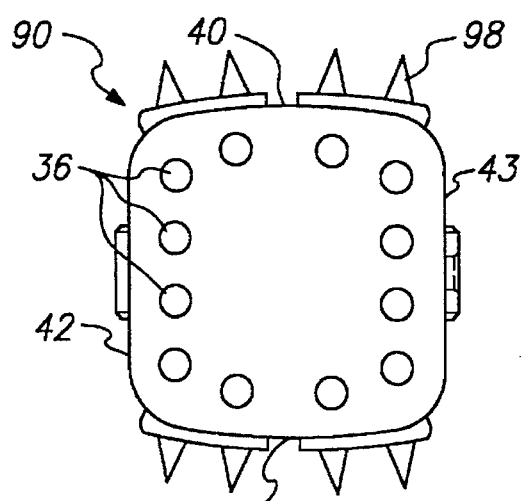

FIG. 4 is a front view of a preferred spinal fixator with the crown portions fully extended.

Figure 5:
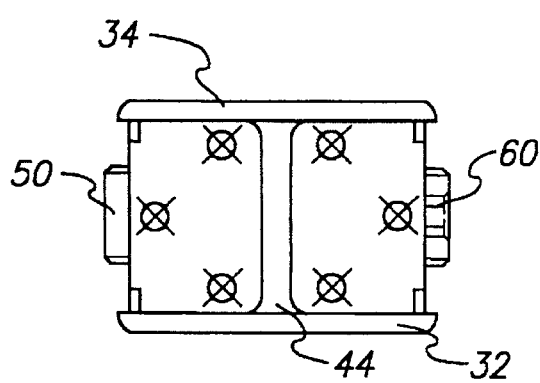

FIG. 5 is a top view of the spinal fixator of FIG. 4.

Figure 6:
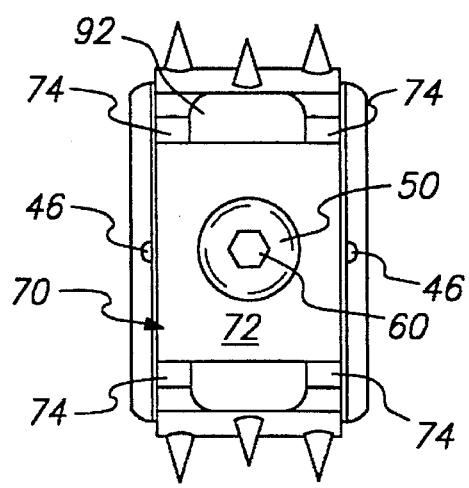

FIG. 6 is a side view of the spinal fixator of FIG. 4 with the crown portions shown fully extended.

Figure 7:
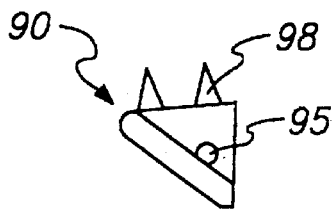

FIG. 7 is a side view of a crown portions of the spinal fixator.

Figure 8:
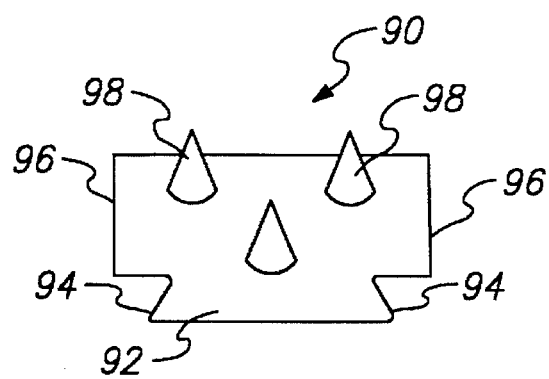

FIG. 8 is a side view in elevation of the crown portion of the spinal fixator showing three teeth and the flange connector.

Figure 9:
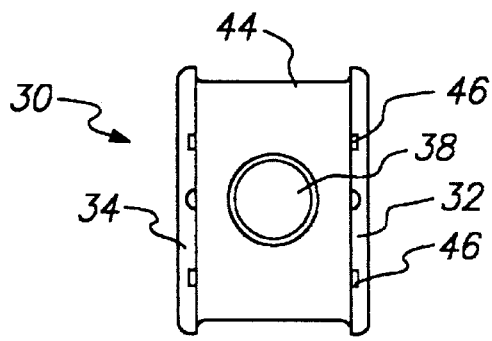

FIG. 9 is a side view of the housing of the spinal fixator.

Figure 10A:
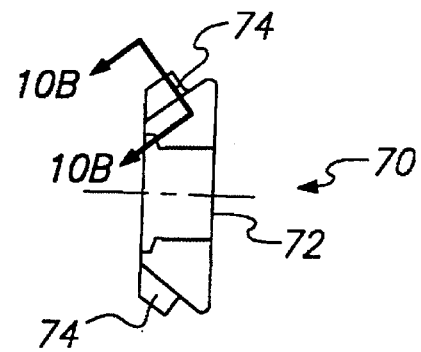
Figure 10B:
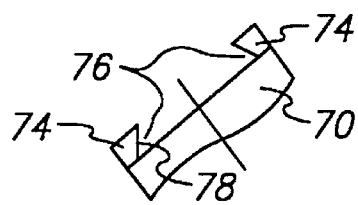

FIGS. 10A and 10B are side and partial sectional views, respectively, of the nut assembly.

Figure 11:
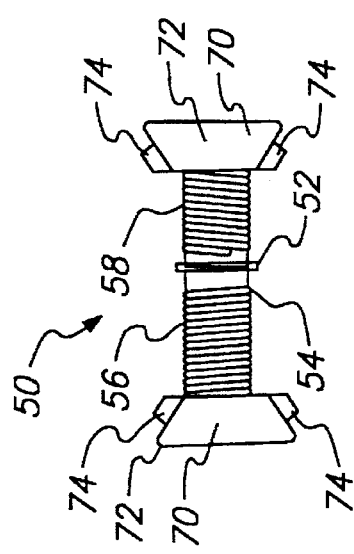

FIG. 11 is a side view of the threaded core and nut assembly.

Figure 12:
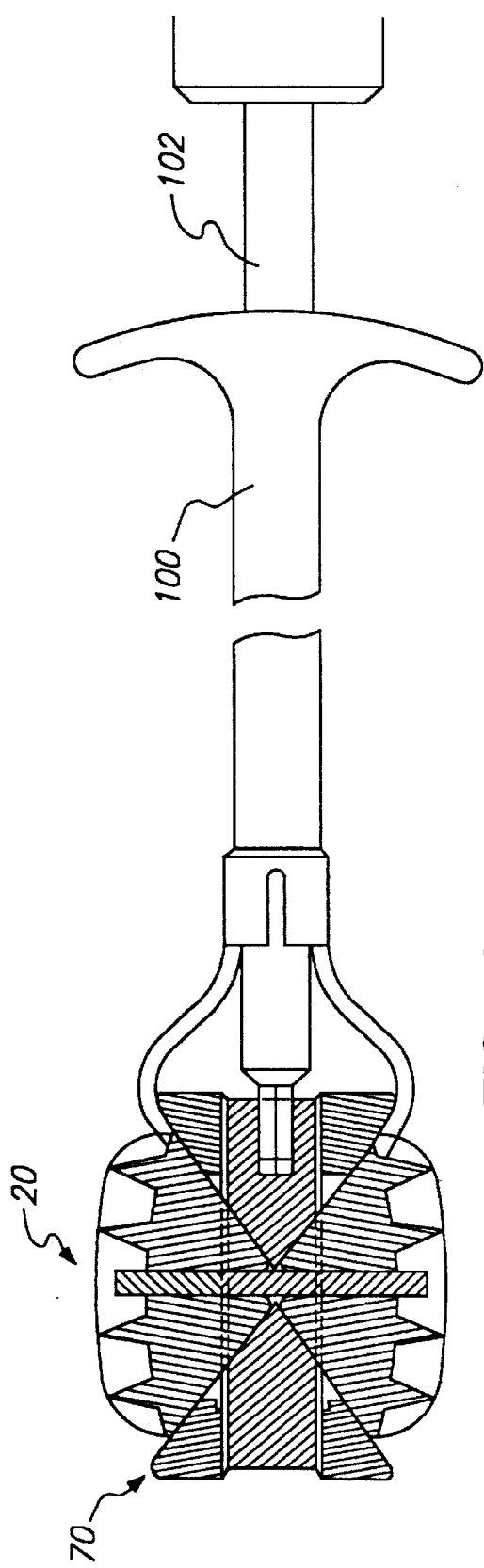

FIG. 12 is a from sectional view of the assembled spinal fixator in its fully retracted position and shown with the insertion tool.

Figure 13:
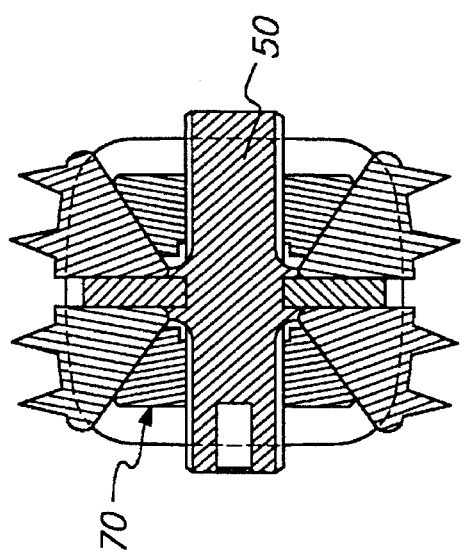

FIG. 13 is a front sectional view of the spinal fixator with the four crowns fully extended.

DESCRIPTION OF PREFERRED EMBODIMENTS

Referring to FIGS. 1 and 2, a spinal fixator embodying the principles of the present invention is shown generally at 20. In FIG. 1, the spinal fixator 20 is shown in side view in its fully retracted, insertion position prior to securing it between the vertebrae 2. The anterio-lateral approach shown in FIG. 1 is preferred for insertion of the fixator 20. In the posterior view shown in FIG. 2, the spinal fixator 20 is shown in its extended position fixed in the concavities of and between the two adjacent vertebrae bodies 4, with the teeth in hidden view.

The spinal fixator 20 is made from a non-corrosive, lightweight metal, titanium 6-4V is preferred, suitable for implanting within the body. When titanium is used for manufacture, postsurgical radiological evaluation is enhanced, but it will be recognized by those skilled in the art that other materials may be used for the spinal fixator, such as surgical quality stainless steel and surgical grade synthetic materials.

Referring now additionally to FIGS. 3-9, the fixator 20 defines a one-piece contoured housing 30 having a front cover 32 which is generally parallel to a back cover 34. All surfaces of the front and back covers 32, 34 are contoured and smooth, and a plurality of openings 36 preferable are provided in the covers 32, 34 to facilitate bony ingrowth. As shown in the aspect of FIG. 3, slots 38 also may be provided through the covers 32, 34. The from and back covers 32, 34 define convex top and bottom crown edges 40, 41. The covers 32, 34 are generally rectangular with the lateral edges 42, 43 being slightly longer than the convex crown edges 40, 41.

A dividing wall 44 extends substantially perpendicular, and substantially centered, between the generally rectangular front and back covers 32, 34, thereby connecting the covers 32, 34. As best shown in FIG. 6 and 9, the inner surface of each of the covers 32, 34 defines one or two notches 46 which extend from the edges 42, 43 to the dividing wall 44 at the center of the covers 32, 34. The purpose of the notches 46 will be made clear below.

Referring now to FIGS. 9 and 11, the dividing wall 44 defines an aperture 38 for mounting an externally threaded core member 50 therethrough. The externally threaded core member 50 defines a substantially centered flange 52 extending from a non threaded area 54. The diameter of the flange 52 is larger than the diameter of the aperture 38 thereby serving as a stop to prevent the core member 50 from passing all the way through the aperture 38. The threads 56 on one half of the core member 50 are oppositely wound from the 58 threads on the remaining half of the core member 50. As best shown in FIG. 6, one end of the core member 50 defines a hex shaped aperture 60. The purpose of the aperture 60 will be made clear below.

Referring now to FIGS. 3, 6, and 10A, 10B, a pair of internally threaded nut assemblies 70 are threaded onto the core member 50 and serve as movable side walls that retract inside the front and back covers 32, 34 of the spinal fixator 20. Each nut assembly 70 defines a planar end wall 72. Extending inwardly at an angle from both the top and the bottom edge of the each of the end walls 72 is a pair of parallel arms 74. Each pair of arms 74 defines a channel 76 with angled, locking side walls 78.

Four crown members 90 are slidably mounted within the four channels 76. Each crown member defines a curved flange 92 which is slidingly engaged in the channel 76 between the paired arms 74. The crown member 92 slides within the channel 76 as the nut assembly 70 moves inwardly or outwardly in response to rotation of the core member 50. The crown members 90 are secured within the fixator by angled edges 94 which engage under and are locked within angled walls 78. Additionally, the crown members 90 are secured by engagement of edges 96 in notches 46. The notches 46 prevent the crown members from rattling against the housing 30 and the nut assemblies 70. Three, substantially equally spaced, conical teeth 98 extend outwardly from the top of each crown member 90. As best shown in FIG. 2, the teeth 98 extend at an angle "A" of approximately 6 degrees from midline "M". It will be recognized by those skilled in the art that the teeth may have other configurations, spacing, and angles; and, that the teeth need not be angled. Angled teeth are preferred to better secure the fixator 20 to the vertebrae 4, particularly to prevent the teeth 98 from loosening, or being dislodged, during spinal extension or flexure.

Referring now to FIGS. 1–2, and 12–13, the spinal fixator 20 is inserted within the concavities between adjacent vertebrae bodies 4 with the patient in an anterio-lateral position, and the fixator 20 in the retracted position shown in FIG. 12. To achieve the retracted position shown in FIG. 12, the core member 50 is rotated to cause the nut assemblies 70 to move outwardly to extend slightly beyond housing walls 42, 43, as shown in FIG. 12, and the crowns slide downwardly in the channels 76 to rest against the dividing wall 44. In the fully retracted position, the teeth 98 are inside of the housing 30, below and above, respectively, the crown edges 40, 41, thereby preventing scraping of the teeth 98 against the vertebral body 4.

A conventional, hollow insertion tool 100 is used to gasp a nut assembly 70 to insert the retracted spinal fixator 20 between the two vertebrae bodies 4. Following placement as in FIG. 1, a tool 102 having a terminus defining a hex configuration is inserted through the insertion tool 100 to engage in aperture 60 in the core member 50. The tool 102 is used to rotate core member 50 to extend the crowns 90 outwardly thereby forcing the teeth 98 into the vertebral body 4. As shown in FIG. 13, rotation of the core member 50 by the tool 102 causes the nut assemblies 70 to retract inside the housing. Retraction of the nut assemblies 70 forces the teeth 98 upward as the flanges 92 slide within the channels 76. As the four separate crown members 90 extend outwardly, the teeth 98 penetrate the vertebral bodies 4. It will be recognized by those skilled in the art that the provision of four, separate crown members 90 enables the fixator 20 to better conform to the contours of the vertebrae. Outward movement of a single crown member 90 may be halted following complete penetration by the teeth 98, and others of the crown members 90 may be further extended upon further rotation of the core member if all of the teeth have not yet penetrated, or fully penetrated the vertebrae. Provision of a plurality of separate crown members enables the fixator to better conform to the anatomy of the vertebrae thereby further securing its position without the need for plates and/or screws. Following placement, the contoured housing, particularly the convex edges 40, 41 follow the contour of the concave vertebral bodies 4, and the bony edges of the vertebral bodies 4 cup the fixator 20.

It is preferred to pack an bone graft, autograft or autograft, around the fixator 20. The openings 36 in the covers 32, 34 permit bony ingrowth of the graft to further secure the position of the fixator 20.

The spinal fixator of the present invention may be made in various sizes to accommodate differing spinal configurations, in particular, to accommodate the smaller spaces between vertebrae typically encountered in children. Heights of preferred retracted fixators of differing sizes vary from approximately 0.75 to 2.0 inches. Heights of fully extended preferred fixators of differing sizes vary from approximately 1.0 to 2.65 inches. Thicknesses of fixators of differing sizes vary from approximately 0.5 to 1.25 inches.

As shown in FIG. 3 in another aspect of the present invention, the covers 32, 34 may define slots 38 for engagement of posts 95 on the crowns 90. In this aspect, the posts 95 prevent the crowns 90 from falling out of the fixator 20 thereby eliminating the need for the mating geometries between the channel edges 78 and the flange 92.

To those skilled in the art to which the present invention pertains, many widely varying embodiments and implementations of the principles of the present invention will be suggested from the foregoing. For instance, the fixator may be used to immobilize other bones besides vertebrae. Accordingly, the contours of the housing may be changed to conform to the contours of other bones. Additionally, any number of teeth may be provided on the crown portions as desired, and fewer or more crown members may be provided. The description and the disclosures present herein are by way of illustration only and should not be considered to limit the present invention, the scope of which is more particularly set forth in the following claims.

What is claimed is:

1. A bone immobilization device for connecting bone to bone comprising:

housing means defining a perimeter;

at least two, separate crown means mounted inside the perimeter of the housing means, each crown means defining at least one outwardly extending tooth means; and means including a core member extending through the housing means and having nut means movably attached to external threads thereon for retracting the at least two, separate crown means inside the perimeter and for extending the at least two, separate crown means outside the perimeter, the at least one tooth means adapted to penetrate bone.

2. The immobilization device of claim 1 wherein the nut means comprises means for mounting the at least two separate crown means, rotation of the core member causing the nut means to move on the external threads to retract into the housing means and move the at least two separate crown means beyond the perimeter, further rotation of the core member causing the nut means to move on the external threads beyond the perimeter to allow the at least two separate crown means to retract inside the perimeter.

3. The immobilization device of claim 2 wherein the external threads on the core member are separated into two, oppositely wound portions, and the core member defines an aperture for insertion of a tool for rotation of the core member.

\* \* \* \* \*